(12) United States Patent
Prince et al.

(10) Patent No.: US 12,059,243 B2
(45) Date of Patent: Aug. 13, 2024

(54) STERILE COVER FOR MEDICAL DEVICES AND METHODS THEREOF

(71) Applicant: Bard Access Systems, Inc., Salt Lake City, UT (US)

(72) Inventors: Matthew J. Prince, Herriman, UT (US); Amir Orome, Sandy, UT (US); Timothy M. Snelling, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 214 days.

(21) Appl. No.: 17/522,828

(22) Filed: Nov. 9, 2021

(65) Prior Publication Data
US 2022/0142502 A1 May 12, 2022

Related U.S. Application Data

(60) Provisional application No. 63/112,056, filed on Nov. 10, 2020.

(51) Int. Cl.
*A61B 5/06* (2006.01)
*A61B 8/00* (2006.01)
(Continued)

(52) U.S. Cl.
CPC ............ *A61B 5/062* (2013.01); *A61M 5/3202* (2013.01); *A61B 8/0841* (2013.01); *A61B 8/4254* (2013.01);
(Continued)

(58) Field of Classification Search
CPC ..... A61B 5/062; A61B 8/0841; A61B 8/4254; A61B 2017/00876; A61B 2562/247
(Continued)

(56) References Cited

U.S. PATENT DOCUMENTS 3,409,853 A 11/1968 Guerth
3,467,926 A 9/1969 Smith
(Continued)

FOREIGN PATENT DOCUMENTS

CN 105025787 A 11/2015
CN 105232047 A 1/2016
(Continued)

OTHER PUBLICATIONS

PCT/US2022/034584 filed Jun. 22, 2022, International Search Report and Written Opinion dated Oct. 10, 2022.
(Continued)

*Primary Examiner* — J. Gregory Pickett
*Assistant Examiner* — Niki M Eloshway
(74) *Attorney, Agent, or Firm* — Rutan & Tucker LLP (57) ABSTRACT

Disclosed herein are devices, systems, and methods thereof for minimizing or preventing contamination of sterile medical devices during magnetization thereof. For example, a magnetizer cover is disclosed for maintaining sterility of a medical device while magnetizing the medical device. The magnetizer cover includes a base, a funnel extending from the base, and a grip tab extending from the base. The base includes a medical-device interface and a magnetizer interface opposite the medical-device interface. The funnel includes a funnel stem configured to protect an elongate medical device from contacting a magnetizer when the medical device is inserted into the funnel. The grip tab is configured for manipulating the magnetizer cover.

28 Claims, 7 Drawing Sheets

(51) Int. Cl.
  *A61M 5/32* (2006.01)
  *A61B 8/08* (2006.01)
  *A61B 17/00* (2006.01)

(52) U.S. Cl.
  CPC .............. *A61B 2017/00876* (2013.01); *A61B 2562/247* (2013.01); *A61M 2205/0272* (2013.01)

(58) Field of Classification Search
  USPC ........................................................ 220/4.01
  See application file for complete search history.

(56) References Cited

U.S. PATENT DOCUMENTS

| | | |
|---|---|---|
| 3,847,157 A | 11/1974 | Caillouette et al. |
| 4,063,561 A | 12/1977 | McKenna |
| 4,161,943 A | 7/1979 | Nogier |
| 4,237,518 A | 12/1980 | Krulwich |
| 4,458,705 A | 7/1984 | Cawood |
| 4,529,954 A | 7/1985 | Steingroever et al. |
| 5,055,813 A | 10/1991 | Johnson |
| 5,659,279 A | 8/1997 | Janssen et al. |
| 5,803,089 A | 9/1998 | Ferre et al. |
| 5,845,646 A | 12/1998 | Lemelson |
| 6,154,352 A | 11/2000 | Atallah |
| 6,249,199 B1 | 6/2001 | Liu |
| 6,310,532 B1 | 10/2001 | Santa Cruz et al. |
| 6,432,036 B1 | 8/2002 | Kim |
| 7,023,309 B2 | 4/2006 | Laskaris et al. |
| 7,090,639 B2 | 8/2006 | Govari |
| 7,135,978 B2 | 11/2006 | Gisselberg et al. |
| 7,214,191 B2 | 5/2007 | Stringer et al. |
| 7,775,215 B2 | 8/2010 | Hassler, Jr. et al. |
| 7,775,966 B2 | 8/2010 | Dlugos et al. |
| 7,850,006 B2 | 12/2010 | Uchiyama |
| 7,873,401 B2 | 1/2011 | Shachar |
| 7,887,516 B2 * | 2/2011 | Young ................ A61B 50/362 604/192 |
| 7,927,270 B2 | 4/2011 | Dlugos et al. |
| 8,016,744 B2 | 9/2011 | Dlugos et al. |
| 8,016,745 B2 | 9/2011 | Hassler, Jr. et al. |
| 8,174,346 B1 | 5/2012 | Koren |
| 8,240,211 B2 | 8/2012 | Zeitner et al. |
| 8,388,541 B2 | 3/2013 | Messerly et al. |
| 8,475,407 B2 | 7/2013 | Kalpin et al. |
| 8,483,802 B2 | 7/2013 | Kalpin et al. |
| 8,532,743 B2 | 9/2013 | Stangenes et al. |
| 8,622,975 B2 | 1/2014 | Andreoni et al. |
| 8,725,435 B2 | 5/2014 | Snow et al. |
| 8,781,555 B2 | 7/2014 | Burnside et al. |
| 8,840,541 B2 | 9/2014 | Snow et al. |
| 8,849,382 B2 | 9/2014 | Cox et al. |
| 8,939,888 B2 | 1/2015 | Augarten et al. |
| 9,017,283 B2 | 4/2015 | Birchard et al. |
| 9,113,812 B2 | 8/2015 | Kalpin et al. |
| 9,155,517 B2 | 10/2015 | Dunbar et al. |
| 9,216,257 B2 | 12/2015 | Kalpin et al. |
| 9,224,529 B2 | 12/2015 | Gery |
| 9,257,220 B2 | 2/2016 | Nicholls et al. |
| 9,299,925 B2 | 3/2016 | Yi et al. |
| 9,308,022 B2 | 4/2016 | Chitre et al. |
| 9,339,601 B2 | 5/2016 | Kalpin et al. |
| 9,439,653 B2 | 9/2016 | Avneri et al. |
| 9,456,766 B2 | 10/2016 | Cox et al. |
| 9,459,087 B2 | 10/2016 | Dunbar et al. |
| 9,492,097 B2 | 11/2016 | Wilkes et al. |
| 9,517,299 B2 | 12/2016 | Tieck et al. |
| 9,521,961 B2 | 12/2016 | Silverstein et al. |
| 9,554,716 B2 | 1/2017 | Burnside et al. |
| 9,597,008 B2 | 3/2017 | Henkel et al. |
| 9,636,031 B2 | 5/2017 | Cox |
| 9,649,048 B2 | 5/2017 | Cox et al. |
| 9,744,291 B2 | 8/2017 | Tieck et al. |
| 10,032,552 B2 | 7/2018 | Ma et al. |
| 10,449,330 B2 | 10/2019 | Newman et al. |
| 10,524,691 B2 | 1/2020 | Newman et al. |
| 10,751,509 B2 | 8/2020 | Misener |
| 11,344,220 B2 | 5/2022 | Burkholz et al. |
| 11,369,410 B2 | 6/2022 | Lindekugel |
| 2003/0040671 A1 | 2/2003 | Somogyi et al. |
| 2003/0052785 A1 | 3/2003 | Gisselberg et al. |
| 2004/0019447 A1 | 1/2004 | Shachar |
| 2004/0051610 A1 | 3/2004 | Sajan |
| 2005/0059884 A1 | 3/2005 | Krag |
| 2006/0114088 A1 | 6/2006 | Shachar |
| 2006/0211914 A1 | 9/2006 | Hassler et al. |
| 2007/0244373 A1 | 10/2007 | Osypka |
| 2007/0290654 A1 | 12/2007 | Govari et al. |
| 2008/0146939 A1 | 6/2008 | McMorrow et al. |
| 2010/0043561 A1 | 2/2010 | Zeitner et al. |
| 2010/0210950 A1 | 8/2010 | Dunbar et al. |
| 2011/0060185 A1 | 3/2011 | Ikuma et al. |
| 2011/0196235 A1 | 8/2011 | Dunbar et al. |
| 2011/0237936 A1 | 9/2011 | Kalpin et al. |
| 2011/0237937 A1 | 9/2011 | Kalpin et al. |
| 2013/0150714 A1 | 6/2013 | Howlett et al. |
| 2013/0296691 A1 | 11/2013 | Ashe |
| 2014/0031674 A1 | 1/2014 | Newman et al. |
| 2014/0165796 A1 | 6/2014 | Gauthier et al. |
| 2014/0253270 A1 | 9/2014 | Nicholls et al. |
| 2014/0257080 A1 | 9/2014 | Dunbar et al. |
| 2014/0257104 A1 | 9/2014 | Dunbar et al. |
| 2014/0257746 A1 | 9/2014 | Dunbar et al. |
| 2015/0080710 A1 | 3/2015 | Henkel et al. |
| 2015/0359991 A1 | 12/2015 | Dunbar et al. |
| 2015/0365787 A1 | 12/2015 | Farrell |
| 2016/0351312 A1 | 12/2016 | Koren |
| 2017/0007200 A1 | 1/2017 | Hagy et al. |
| 2017/0079549 A1 | 3/2017 | Henkel et al. |
| 2017/0079550 A1 | 3/2017 | Henkel et al. |
| 2017/0079551 A1 | 3/2017 | Henkel et al. |
| 2017/0126864 A1 | 5/2017 | Lim et al. |
| 2017/0261564 A1 | 9/2017 | Gabrys et al. |
| 2017/0325713 A1 * | 11/2017 | Burkholz ................ A61M 5/32 |
| 2017/0326342 A1 * | 11/2017 | Ma ...................... A61M 5/1626 |
| 2018/0061546 A1 * | 3/2018 | Ma ........................ H01F 13/003 |
| 2018/0289929 A1 * | 10/2018 | Ma ...................... A61M 5/3202 |
| 2018/0310955 A1 * | 11/2018 | Lindekugel ............ A61B 90/98 |
| 2019/0298221 A1 * | 10/2019 | Sonderegger ...... A61M 25/0108 |
| 2020/0360662 A1 | 11/2020 | Ma et al. |
| 2021/0065857 A1 | 3/2021 | Newman et al. |
| 2021/0169585 A1 | 6/2021 | Prince et al. |
| 2022/0105324 A1 * | 4/2022 | Broniec ................ A61M 29/00 |
| 2022/0142501 A1 | 5/2022 | Prince et al. |
| 2022/0323101 A1 | 10/2022 | Lindekugel et al. |
| 2022/0401158 A1 | 12/2022 | Sowards et al. |
| 2023/0006443 A1 | 1/2023 | Patankar et al. |

FOREIGN PATENT DOCUMENTS

| | | |
|---|---|---|
| CN | 103945772 B | 9/2016 |
| CN | 105073067 B | 6/2017 |
| DE | 102006033229 B4 | 5/2013 |
| EP | 2015105 B1 | 6/2011 |
| EP | 2730306 A1 | 5/2014 |
| EP | 2285287 B1 | 4/2015 |
| EP | 2939599 A2 | 11/2015 |
| EP | 2939601 A2 | 11/2015 |
| EP | 2997901 A1 | 3/2016 |
| EP | 2753243 B1 | 4/2016 |
| JP | 5349582 B2 | 11/2013 |
| JP | 5908981 B2 | 4/2016 |
| JP | 6242421 B2 | 12/2017 |
| KR | 20150123233 A | 11/2015 |
| WO | 2008009442 A2 | 1/2008 |
| WO | 2009010386 A1 | 1/2009 |
| WO | 2009129845 A1 | 10/2009 |
| WO | 2013034175 A1 | 3/2013 |
| WO | 2013142386 A1 | 9/2013 |
| WO | 2014062728 A1 | 4/2014 |
| WO | 2014135592 A1 | 9/2014 |
| WO | 16096190 A1 | 6/2016 |
| WO | 17016961 A1 | 2/2017 |

(56) References Cited

FOREIGN PATENT DOCUMENTS

| WO | 2018/201053 A1 | 11/2018 |
| WO | 2022/099147 A1 | 5/2022 |
| WO | 2022103772 A1 | 5/2022 |
| WO | 2022271864 A1 | 12/2022 |
| WO | 2023009446 A1 | 2/2023 |

OTHER PUBLICATIONS

PCT/US2022/038202 filed Jul. 25, 2022 International Search Report and Written Opinion dated Nov. 14, 2022.
EP 18790656.5 filed Nov. 27, 2019 Supplementary European Search Report dated Apr. 9, 2020.
EP 221711096 filed May 2, 2022, Extended European Search Report dated Jul. 22, 2022.
EP20202521.9 filed Oct. 19, 2020 Extended European Search Report dated Jan. 28, 2021.
PCT/US2018/029958 filed Apr. 27, 2018 Communication Pursuant to Rules 70(2) and 70a(2) dated Apr. 29, 2020.
PCT/US2018/029958 filed Apr. 27, 2018 International Search Report and Written Opinion dated Jul. 11, 2018.
PCT/US2018/029958 filed Apr. 27, 2018 International Search Report dated Apr. 27, 2018.
PCT/US2021/058478 filed Nov. 8, 2021 International Search Report and Written Opinion dated Mar. 1, 2022.
U.S. Appl. No. 15/965,419, filed Apr. 27, 2018 Final Office Action dated Jan. 15, 2021.
U.S. Appl. No. 15/965,419, filed Apr. 27, 2018 Non-Final Office Action dated Aug. 6, 2021.
U.S. Appl. No. 15/965,419, filed Apr. 27, 2018 Non-Final Office Action dated Sep. 24, 2020.
U.S. Appl. No. 15/965,419, filed Apr. 27, 2018 Notice of Allowance dated Feb. 16, 2022.
PCT/US2021/058667 filed Nov. 9, 2021 International Search Report and Written Opinion dated Mar. 1, 2022.
U.S. Appl. No. 17/521,680, filed Nov. 8, 2021 Non-Final Office Action dated Jun. 2, 2023.
U.S. Appl. No. 17/521,680, filed Nov. 8, 2021 Notice of Allowance dated Oct. 11, 2023.

* cited by examiner

STERILE COVER FOR MEDICAL DEVICES AND METHODS THEREOF

PRIORITY

This application claims the benefit of priority to U.S. Patent Application No. 63/112,056, filed Nov. 10, 2020, which is incorporated by reference in its entirety into this application.

BACKGROUND

Ultrasound imaging is a widely accepted tool for guiding interventional medical devices to target locations in blood vessels or organs within the human body. A medical device such as a needle can be magnetized, inserted into the body by way of a percutaneous puncture, and tracked in real-time both immediately before and after the puncture so a clinician can determine the distance and the orientation of the needle to a target location and ensure successful access thereto.

One problem that can arise while tracking a medical device or preparing to do so is loss of sterility of the medical device by contact with one or more contaminated surfaces. Indeed, a medical device can be magnetized by movement through a magnetizer containing one or more magnetization elements. However, while the medical device and any contact that the user makes with the medical device (e.g., via sterilized gloves) can be sterilized, the magnetization device and its components cannot be sterilized leading to the one-or-more contaminated surfaces. Exposure or contact by the medical device or the user to the one-or-more contaminated surface can result in the loss of sterility. For example, contact by the medical device or the user's gloves with the magnetizer could result in contaminants on the magnetizer contaminating the contacting object.

What is needed are devices, systems, and methods thereof for minimizing or preventing contamination of sterile medical devices during magnetization.

SUMMARY

Disclosed herein is a magnetizer cover for maintaining sterility of a medical device while magnetizing the medical device. The magnetizer cover includes a base, a funnel extending from the base, and a grip tab extending from the base. The base includes a medical-device interface and a magnetizer interface opposite the medical-device interface. The funnel includes a funnel stem configured to protect an elongate medical device from contacting a magnetizer when the medical device is inserted into the funnel. The grip tab is configured for manipulating the magnetizer cover.

In some embodiments, at least the base includes one or more structural stability ridges incorporated therein. The one-or-more structural stability ridges provide added structural stability to the magnetizer cover.

In some embodiments, the grip tab extends from the base in a same direction as the one-or-more structural stability ridges incorporated into the base.

In some embodiments, the base and funnel are configured to intervene between the magnetizer and the medical device to prevent the medical device from touching the magnetizer and contaminating the medical device.

In some embodiments, the magnetizer cover further includes a side barrier orthogonal to the base. The side barrier is configured to intervene between the magnetizer and the medical device to prevent the medical device from touching the magnetizer and contaminating the medical device.

In some embodiments, the grip tab extends from the base opposite the side barrier.

In some embodiments, the funnel extends from the magnetizer interface of the base enabling the funnel stem to insert into a magnetizer aperture of the magnetizer.

In some embodiments, the funnel further includes a funnel mouth between the base and the funnel stem. The funnel mouth is configured to direct the medical device into the funnel stem.

In some embodiments, a length of the funnel is greater than a length of a magnetizable portion of the medical device.

In some embodiments, the funnel stem has an open end opposite the base.

In some embodiments, the funnel stem has a closed end opposite the base.

In some embodiments, the funnel stem includes one or more inwardly facing prongs extending into the funnel stem from the funnel mouth. The one-or-more prongs are configured to catch a cover over the medical device when the medical device is inserted into the funnel with the cover thereover. The one-or-more prongs are also configured to prevent the cover from being withdrawn from the funnel when the medical device is withdrawn from the funnel.

In some embodiments, the grip tab includes a plurality of transverse ridges on a same face as the medical-device interface of the base.

In some embodiments, the grip tab further includes the transverse ridges on a same face as the magnetizer interface of the base.

Also disclosed herein is a magnetizing system for maintaining sterility of a medical device while magnetizing the medical device. The system includes a magnetizer and a magnetizer cover. The magnetizer includes a magnetizer aperture and a magnetization chamber. The magnetizer aperture is formed in a cover interface of the magnetizer. The magnetization chamber is accessible through the magnetizer aperture. The magnetizer cover includes a base, a funnel extending from the base, and a grip tab extending from the base. The base includes a medical-device interface and a magnetizer interface opposite the medical-device interface. The funnel includes a funnel stem configured to protect an elongate medical device from contacting the magnetizer when the medical device is inserted into the funnel. The grip tab is configured for manipulating the magnetizer cover.

In some embodiments, at least the base includes one or more structural stability ridges incorporated therein. The one-or-more structural stability ridges provide added structural stability to the magnetizer cover.

In some embodiments, the grip tab extends from the base in a same direction as the one-or-more structural stability ridges incorporated into the base.

In some embodiments, the base and funnel are configured to intervene between the magnetizer and the medical device to prevent the medical device from touching the magnetizer and contaminating the medical device.

In some embodiments, the magnetizer cover further includes a side barrier orthogonal to the base. The side barrier is configured to intervene between the magnetizer and the medical device to prevent the medical device from touching the magnetizer and contaminating the medical device.

In some embodiments, the grip tab extends from the base opposite the side barrier.

In some embodiments, the funnel extends from the magnetizer interface of the base enabling the funnel stem to insert into the magnetizer aperture of the magnetizer.

In some embodiments, the funnel further includes a funnel mouth between the base and the funnel stem. The funnel mouth is configured to direct the medical device into the funnel stem.

In some embodiments, a length of the funnel is greater than a length of a magnetizable portion of the medical device.

In some embodiments, the funnel stem has an open end opposite the base.

In some embodiments, the funnel stem has a closed end opposite the base.

In some embodiments, the funnel stem includes one or more inwardly facing prongs extending into the funnel stem from the funnel mouth. The one-or-more prongs are configured to catch a cover over the medical device when the medical device is inserted into the funnel with the cover thereover. The one-or-more prongs are also configured to prevent the cover from being withdrawn from the funnel when the medical device is withdrawn from the funnel.

In some embodiments, the grip tab includes a plurality of transverse ridges on a same face as the medical-device interface of the base.

In some embodiments, the grip tab further includes the transverse ridges on a same face as the magnetizer interface of the base.

Also disclosed herein is a method for maintaining sterility of an elongate medical device while magnetizing the medical device. The method includes a magnetizer cover-applying operation, a medical device-inserting operation, and a magnetization-initiating operation. The magnetizer cover-applying operation includes inserting at least a funnel stem of a funnel of a magnetizer cover into a magnetizer aperture of a magnetizer, thereby disposing the funnel stem in a magnetization chamber of the magnetizer. The medical device-inserting operation includes inserting a magnetizable portion of the medical device into the funnel stem of the magnetizer cover. The funnel stem is configured to protect the magnetizable portion of the medical device from contacting the magnetizer. The magnetization-initiating operation includes initiating magnetization of the medical device.

In some embodiments, the magnetizable portion of the medical device includes a cover thereover. In addition, the funnel stem includes one or more inwardly facing prongs extending into the funnel stem from a funnel mouth of the funnel. The one-or-more prongs catch the cover during the medical device-inserting operation when inserting the magnetizable portion of the medical device into the funnel stem.

In some embodiments, the method further includes a medical device-withdrawing operation. The medical device-withdrawing operation includes withdrawing the medical device from the funnel stem after magnetization of the medical device is complete. The one-or-more prongs prevent the cover from being withdrawn from the funnel stem with the medical device, thereby retaining the cover in the funnel stem.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures can be made from the particular embodiments disclosed herein without departing from the scope of the concepts provided herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," or a "proximal portion" of, for example, a medical device disclosed herein includes a portion of the medical device intended to be relatively nearer to a designated location. Likewise, a "proximal length" of, for example, the medical device includes a length of the medical device intended to be relatively nearer to or in the designated location. A "proximal end" of, for example, the medical device includes an end of the medical device intended to be relatively nearer to the designated location. The proximal portion, the proximal-end portion, or the proximal length of the medical device can include the proximal end of the medical device; however, the proximal portion, the proximal-end portion, or the proximal length of the catheter need not include the proximal end of the medical device. That is, unless context suggests otherwise, the proximal portion, the proximal-end portion, or the proximal length of the medical device is not a terminal portion or terminal length of the medical device.

With respect to "distal," or a "distal portion" of, for example, a medical device disclosed herein includes a portion of the medical device intended to be relatively further from a designated location. Likewise, a "distal length" of, for example, the medical device includes a length of the medical device intended to be relatively further from the designated location. A "distal end" of, for example, the medical device includes an end of the medical device intended to be relatively further from the designated location. The distal portion, the distal-end portion, or the distal length of the medical device can include the distal end of the medical device; however, the distal portion, the distal-end portion, or the distal length of the medical device need not include the distal end of the medical device. That is, unless context suggests otherwise, the distal portion, the distal-end portion, or the distal length of the catheter is not a terminal portion or terminal length of the medical device.

Unless defined otherwise, all technical and scientific terms used herein have the same meaning as commonly understood by those of ordinary skill in the art.

As set forth above, devices, systems, and methods thereof are needed to minimize or prevent contamination of sterile medical devices during magnetization. Disclosed herein are those devices, systems, and methods thereof.

Magnetizer Covers

Figure 1:
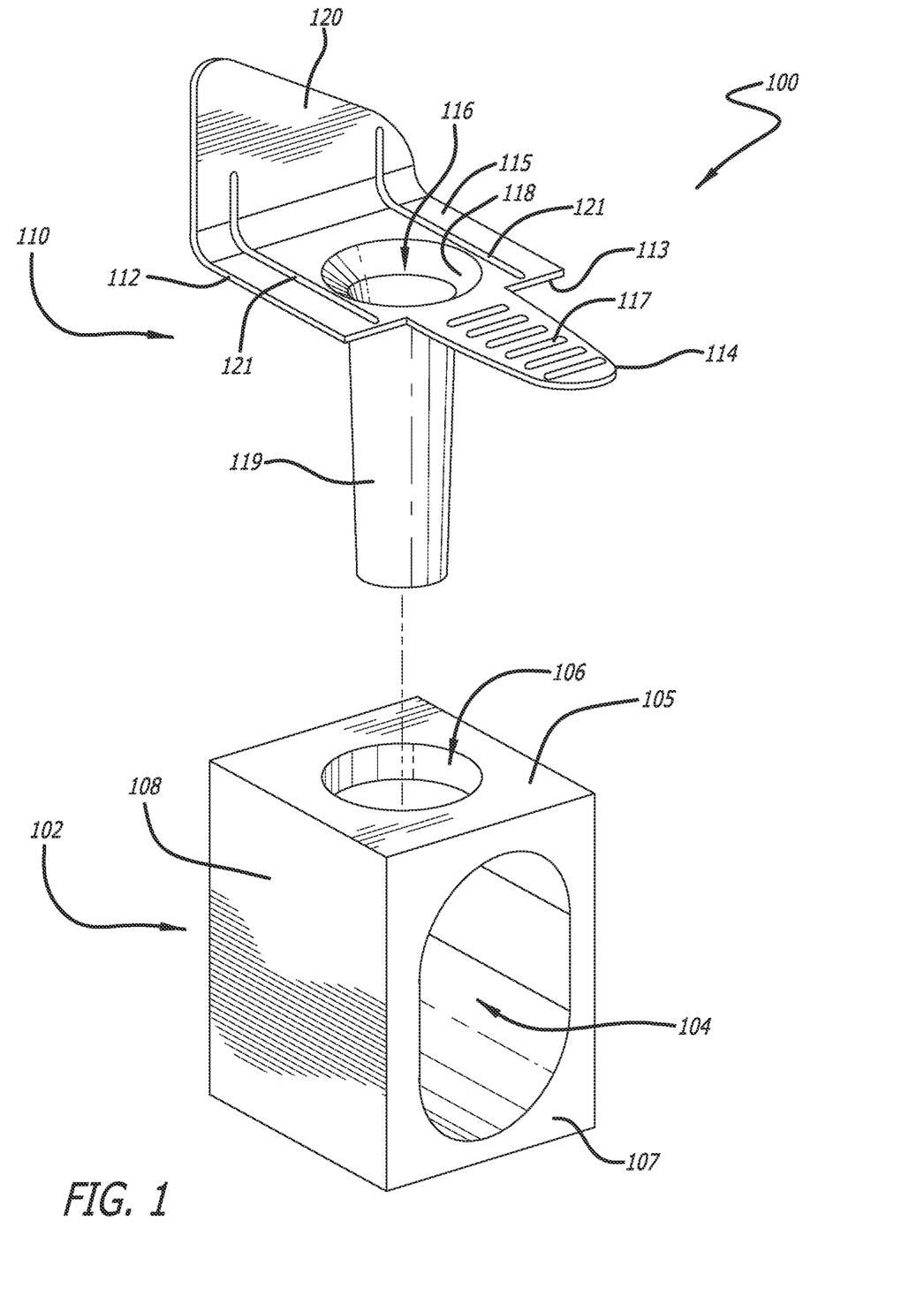
FIG. 1 illustrates a magnetization system including a magnetizer and magnetizer cover in accordance with some embodiments.

Referring to FIG. 1, a magnetization system 100 including a magnetizer 102 and a magnetizer cover 110 is illustrated in accordance with some embodiments. In some embodiments, the magnetizer 102 and the magnetizer cover 110 can be implemented with magnetic-based medical-device guidance systems for insertion and detection of medical devices (e.g., a magnetic-based needle guidance system for insertion and detection of sterilized needles). Examples of magnetic-based medical-device guidance systems are disclosed in U.S. Pat. Nos. 8,388,541; 8,781,555; 8,849,382; 9,456,766; 9,492,097; 9,521,961; 9,554,716; 9,636,031; 9,649,048; 10,449,330; 10,524,691; and 10,751,509, each of which is incorporated by reference in its entirety into this application.

As shown, the magnetizer 102 can include a magnetization chamber 104, a cover interface 105 including a magnetizer aperture 106 therethrough, an open face 107, and a magnetization element 108. The magnetizer cover 110 can include a base 112, a magnetizer interface 113, a grip tab 114, a medical-device interface 115, a funnel 116 including a funnel mouth 118 and a funnel stem 119, and a side barrier 120.

It is appreciated that a medical device of a magnetizable material enables the medical device (e.g., a needle) to be magnetized, which, in turn, can be tracked by an ultrasound-imaging system when the magnetized medical device is brought into proximity of magnetic sensors (e.g., a magnetic-sensor array) or inserted into a body of a patient during an ultrasound-based medical procedure. Such magnetic-based tracking of the magnetized medical device assists a clinician in placing a tip of the medical device in a desired location, such as in a lumen of a blood vessel, by superimposing a simulated needle image representing the real-time distance and orientation of the needle over an ultrasound image of the body of the patient being accessed by the magnetized medical device. Such a medical device can be, e.g., stainless steel; however, other suitable needle materials that are capable of being magnetized can be employed. So configured, the needle or the like can produce a magnetic field or create a magnetic disturbance in a magnetic field detectable as magnetic signals by the magnetic-sensor array of the ultrasound probe so as to enable the distance and orientation of the magnetized medical device to be tracked by the ultrasound-imaging system.

In the embodiment of FIG. 1, the magnetizer 102 includes a housing comprising the magnetization chamber 104 and a plurality of faces, including the cover interface 105 and the open face 107. The magnetizer interface 113 of the magnetizer cover 110 is configured to contact the cover interface 105 of the magnetizer 102 as set forth below. The cover interface 105 includes the magnetizer aperture 106, through which the funnel 116 or the funnel stem 119 thereof can be inserted. In an example, the magnetizer aperture 106 can be an at least substantially circular aperture shaped by the cover interface 105. The magnetizer aperture 106 allows the magnetizer cover 110, as described herein, to be at least partially inserted into the magnetization chamber 104 of the magnetizer 102 so that objects, such as medical devices (e.g., sterilized needles) can be placed within the magnetizer cover 110 to be magnetized while being protected from exposure to contaminants.

In one embodiment, a user positions the sterilized magnetizer cover 110 so that the funnel 116 or the funnel stem 119 thereof fits within the magnetizer 102. For example, the funnel stem 119 of the magnetizer cover 110 can be inserted into the magnetization chamber 104 through the magnetizer aperture 106 formed by the cover interface 105. The magnetizer 102 can be unsterilized. The funnel stem 119 is configured to fit within the magnetizer aperture 106 so that the magnetizer cover 110 is stabilized and retained by the magnetizer 102 and does not shift or change position. The user then moves a sterilized, magnetizable medical device (e.g., needle) through the funnel mouth 118 of the magnetizer cover 110, causing or directing the medical device to be moved into at least part of the funnel stem 119 (i.e., at least partially within the magnetizer cover 110) while the funnel stem 119 is inserted within the magnetizer 102. The medical device is then magnetized by the magnetizer 102. The user then removes the medical device from the magnetization system 100 for use with an ultrasound imaging system. Before, during, and after movement through the magnetizer 102, the sterilized medical device can make contact with the sterilized the magnetizer cover 110 without contacting the unsterilized magnetizer 102.

In the embodiment of FIG. 1, the magnetizer cover 110 includes the grip tab 114. A user can hold the grip tab 114 to position the magnetizer cover 110 on the magnetizer 102 while maintaining the sterility of other surfaces. For example, the user can hold, carry, or place the magnetizer cover 110 using the grip tab 114. The grip tab 114 can be integrated into the base 112 of the magnetizer 102 (e.g., the base 112 can comprise the grip tab 114). The grip tab 114 can extend or protrude from the base 112. As described below, the grip tab 114 can include structures further enabling the user to manipulate the magnetizer cover 110.

The magnetizer cover 110 of FIG. 1 includes the base 112 having the magnetizer interface 113. In the embodiment of FIG. 1, the base 112 is at least partially planar. The magnetizer interface 113 is configured so that at least a portion of the magnetizer interface 113 can be positioned on at least a portion of the cover interface 105 of the magnetizer 102. For example, the magnetizer interface 113 can rest on the cover interface 105.

Among other things, the magnetizer cover 110 allows medical devices (e.g., needles) to be magnetized by the magnetizer 102 without exposing the medical device to potentially contaminating surfaces of the magnetizer 102. In examples, the magnetizer cover 110 can be a sheath, barrier, case, envelope, wrapper or other structure to prevent or impede surfaces of the magnetizer 102 from contacting an object inserted into the magnetizer 102. The magnetizer cover 110 can be constructed from any suitable sterilizable material such as, but not limited to, medical-grade plastics or silicone.

In some embodiments, the magnetizer interface 113 can be configured to securely fit or attach to the magnetizer 102, so that the base 112 and, more generally, the magnetizer cover 110 does not shift or move while the magnetizer interface 113 rests on the cover interface 105. For example, the magnetizer interface 113 can include one or more roughened portions which impede the magnetizer cover 110 from moving while positioned on the magnetizer 102. Furthermore, in some embodiments, the magnetizer cover 110 includes sterilized structures which function to stabilize or align the magnetizer cover 110. For example, in the embodiment of FIG. 1, a portion of the magnetizer cover 110 orthogonal to the base 112 forms the side barrier 120. The side barrier 120 can be configured to align with a portion of the magnetizer 102 or other structure, such as by pressing against another object, thereby providing a barrier against the other object for maintaining a sterile field about the medical-device interface 115. As shown in FIG. 1, one or more structural stability ridges 121 can be incorporated into at least the base 112 to provide added stability to the magnetizer cover 110. In addition, the one-or-more structural stability ridges 121 can be incorporated into the side barrier 120 such that the one-or-more structural stability ridges 121 extend along the base 112 and into the side barrier 120 for even more added stability to the magnetizer cover 110.

In some embodiments, at least some of the components of the magnetizer cover 110 are sterilized. For example, the base 112, the magnetizer interface 113, the grip tab 114, the medical-device interface 115, the funnel 116, and the side barrier 120 can be sterilized. A medical device that is moved or placed within the magnetizer cover 110 will therefore only touch the sterilized surfaces of the magnetizer cover 110, thereby retaining the sterility of the medical device. Furthermore, a user with sterile gloves can touch sterilized surfaces of the magnetizer cover 110 without loss of glove sterility.

The base 112 of FIG. 1 includes the funnel 116 with the funnel mouth 118 and the funnel stem 119 extending therefrom. A medical device to be magnetized can enter the magnetizer cover 110 through the funnel mouth 118 and move within the funnel stem 119. In some embodiments, the funnel stem 119 is at least as long as the medical device, thereby reducing the chance that the medical device will contact the magnetizer 102.

The funnel stem 119 can be straight (e.g., at least substantially perpendicular to the base 112), or can be angled. When angled, the funnel stem 119 can have an angle of, for example, 15°, 30°, 45°, 60°, 75°, 90°, etc. The funnel stem 119 can include an open end or a closed end. In embodiments in which the funnel stem 119 has an open end, a sterilized end piece can be coupled thereto to create a closed end. A closed end and a sterilized end piece each prevent a magnetizable medical device within the funnel stem 119 from contacting the magnetizer 102, and thus minimizes the risk of contamination. In some embodiments, the sterilized end piece can be omitted. For example, in embodiments wherein the length of the funnel stem 119 is greater than a length of a needle, the needle can be magnetized without utilizing a sterilized end piece. In some embodiments, the sterilized end piece can be removable.

In some embodiments, the funnel mouth 118 can be a hole, aperture, gap, slot or other opening formed in the base 112 that permits a medical device to enter and move through the magnetizer cover 110. The funnel stem 119 can comprise one or more of a tube, a shaft, or a bore. In some embodiments, the funnel mouth 118 can have a gradually sloping edge, which recedes, the sloping edge configured to direct the medical device into the funnel stem 119 as well as center the medical device in the magnetizer cover 110. In further embodiments, the funnel mouth 118 can have an edge which is not gradually sloped.

In some embodiments, the funnel mouth 118 and the funnel stem 119 can have different shapes than illustrated. For example, in an embodiment the funnel stem 119 can be tapered. In another embodiment, the funnel stem 119 can be straight or substantially straight.

The funnel stem 119 can be shaped according to the shape of a corresponding medical device. For example, in embodiments in which the medical device is a needle, the funnel stem 119 can be shaped substantially to facilitate movement of the needle into and out of the magnetizer cover 110 (e.g., cylindrically). However, the shape of each of the funnel mouth 118 and the funnel stem 119 is not limited to that illustrated. Instead, in some embodiments, the funnel mouth 118 can have a rectangular opening or the funnel stem 119 can be a rectangular prism (a cuboid).

In some embodiments, the funnel stem 119 is hollow. For example, the funnel stem 119 can be void of structures that would impede the passage of a medical device (e.g., needle) therethrough.

The funnel mouth 118 and the funnel stem 119 of the funnel 116 of the magnetizer cover 110 can be configured according to various characteristics of the medical device being magnetized. For example, in embodiments where the medical device to be magnetized is a needle, the funnel mouth 118 and the funnel stem 119 can each have a width which is at least equal to a width of the needle, so that the needle can pass through. In some embodiments, each of the funnel mouth 118 and the funnel stem 119 are wider than the needle, to facilitate movement of the needle into and out of the magnetizer cover 110. The funnel mouth 118 and the funnel stem 119 can have different widths from each other. For example, the funnel mouth 118 can be wider than the funnel stem 119 so that a medical device can enter the magnetizer cover 110 but will be less likely to unintentionally pass through.

In the embodiment of FIG. 1, the magnetization chamber 104 includes multiple sides. At least a portion of one or more of the sides of the magnetization chamber 104 can have material removed to facilitate operation of the magnetizer 102. For example, as shown in the embodiment of FIG. 1, a portion of the side of the magnetization chamber 104 can be removed providing the open face 107. Among other things, through the open face 107 a user can view the interior of the magnetizer 102 or the magnetization element 108 thereof, clean the interior of the magnetizer 102 or the magnetization element 108 thereof, view the magnetizer cover 110 and confirm its placement in the magnetizer 102, remove unwanted objects, or replace objects within the magnetizer 102.

Figure 2:
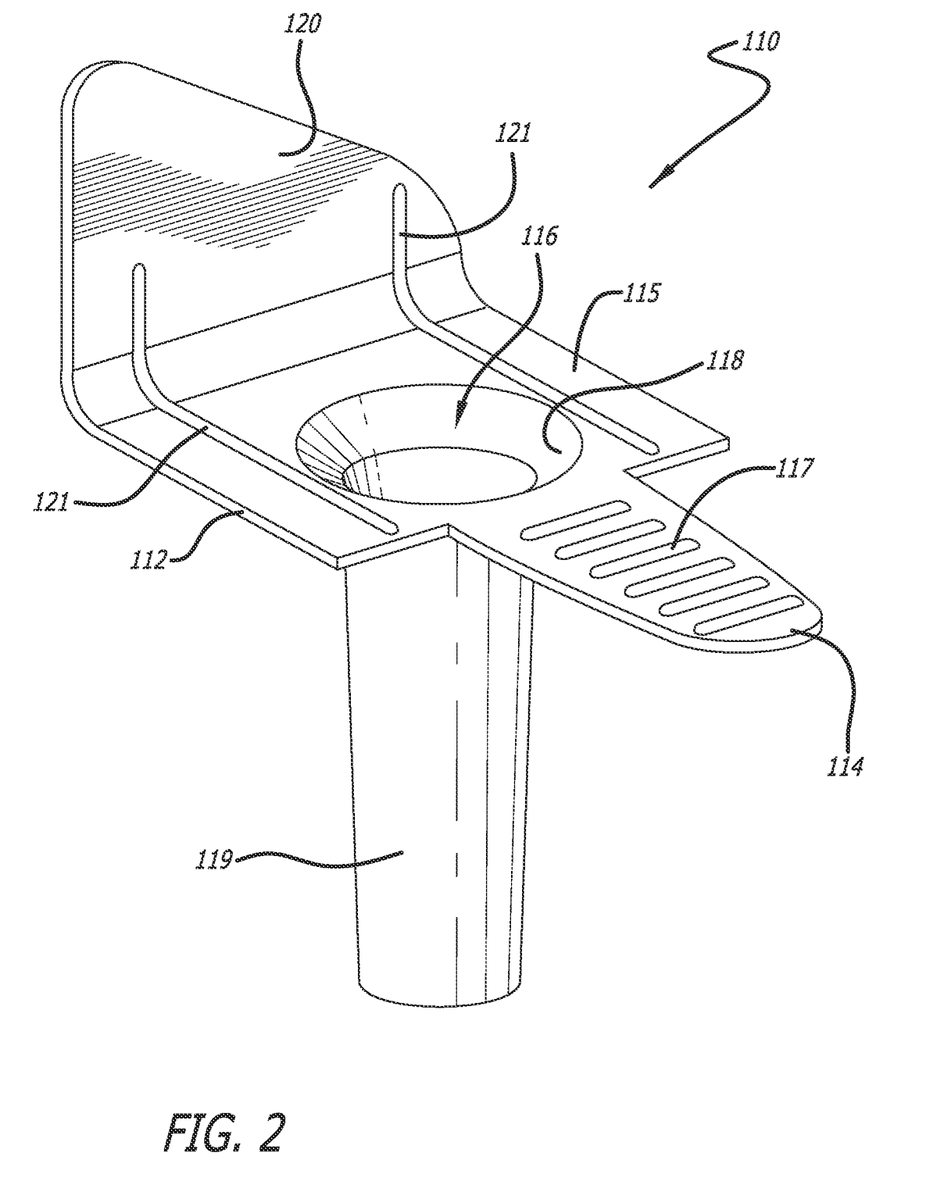
FIG. 2 illustrates a magnetizer cover in accordance with some embodiments.

Referring to FIG. 2, the magnetizer cover 110 generally includes the magnetizer interface 113, the grip tab 114, the funnel 116 including the funnel mouth 118 and the funnel stem 119, and the side barrier 120. In an embodiment, a user places the magnetizer cover 110 at a desired location with the grip tab 114, inserts the funnel 116 or the funnel stem 119 thereof into the magnetizer 102, and inserts a magnetizable medical device into the funnel 116 through funnel mouth 118. The magnetizer cover 110 is retained in the magnetizer 102 by the funnel stem 119 and gravity. The medical device is magnetized while in the funnel 116 and then removed by the user.

In some embodiments, the magnetizer cover 110 can be configured to facilitate user insertion and removal of the medical device (e.g., the needle) into the magnetizer 102, as well as any covers (e.g., the needle cover 506 for the needle 500) for the medical device. For example, the funnel mouth 118 can have a width, and funnel stem 119 can have a depth, suitable for enabling a user to briefly insert and remove a needle in a dipping motion, thereby magnetizing the needle within the magnetizer 102. In further embodiments, the funnel mouth 118 and the funnel stem 119 can have proportions which are suitable for insertion of either a needle, or a needle having a needle cover. The magnetizer cover 110 can then be used even if the needle cover has not been removed from a needle.

The magnetizer interface 113 of the magnetizer cover 110 can have a shape and size for placement on the magnetizer 102. In some embodiments, the magnetizer interface 113 can rest on the magnetizer 102 or the cover interface 105 thereof after insertion of the funnel 116 or the funnel stem 119 thereof through the magnetizer aperture 106 such that the magnetizer interface 113 contacts or touches the cover interface 105 while the medical-device interface 115 does not contact or touch the magnetizer 102 in any way. The magnetizer cover 110 can be secured by insertion of the funnel stem 119 of the funnel 116 into the magnetizer aperture 106 of the magnetizer 102, which minimizes movement and accidental removal of the magnetizer cover 110. In some embodiments, the magnetizer interface 113 can include further securing features (e.g., latches, locks, or rims) to prevent movement of the magnetizer cover 110 while inserted in the magnetizer 102. In some embodiments, the cover interface 105 can include further securing features (e.g., latches, locks, or rims) to prevent movement of the magnetizer cover 110 while inserted in the magnetizer 102. In some embodiments, a medical device can be inserted to fit tightly with the medical-device interface 115 so that when the medical device is removed, the magnetizer cover 110 is also removed with the medical device remaining fitted within the medical-device interface 115 (see FIGS. 5C-5F).

The grip tab 114 can include a gripping feature 117. In the embodiment of FIG. 2, the grip tab 114 is an extension of the base 112, shaped for a user to manipulate the magnetizer cover 110 such as to pick up the magnetizer cover 110 for insertion into the magnetizer 102. While the grip tab 114 of FIG. 2 is at least substantially planar to the base 112, in some embodiments, the grip tab 114 can be angled, shaped or have a form factor to enable a user to manipulate the magnetizer cover 110 without touching portions of the magnetizer cover 110 other than the grip tab 114 and the gripping feature 117 thereof. In some embodiments, the grip tab 114 can further include a handle; an extended tab; and/or a bar. The grip tab 114 can have a length extending over an edge of the magnetizer 102 by a predefined length, so that the grip tab 114 can be held (e.g., between thumb and forefinger) and the magnetizer cover 110 can be placed by a user without at least a portion of the grip tab 114 touching the magnetizer 102.

Figure 4A:
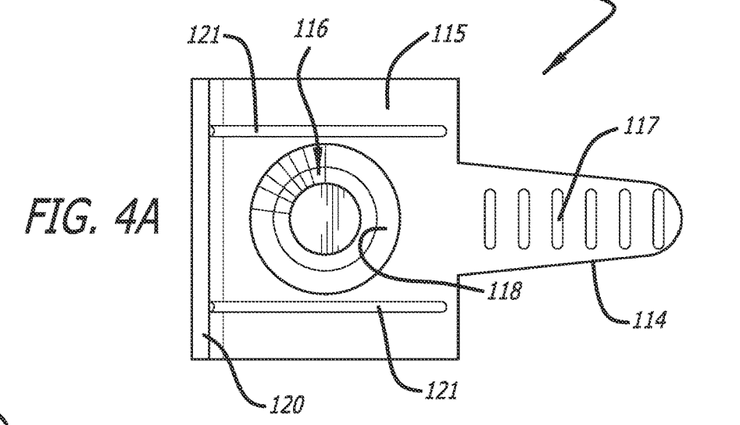
FIG. 4A illustrates a top view of the magnetizer cover in accordance with some embodiments.
Figure 4B:
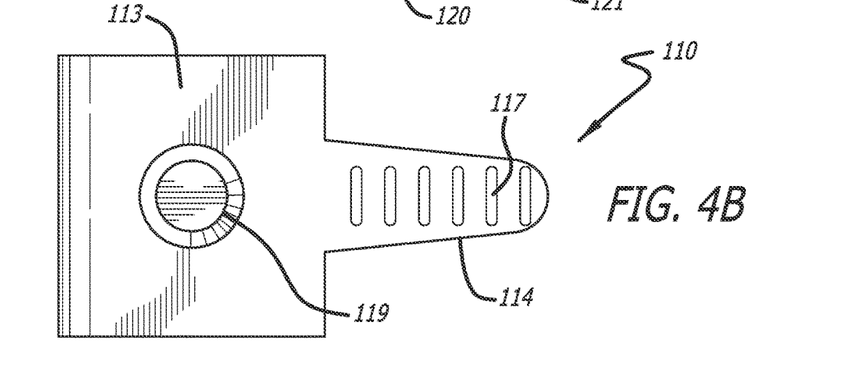
FIG. 4B illustrates a bottom view of the magnetizer cover in accordance with some embodiments.

The gripping feature 117 can assist a user in handling the magnetizer cover 110 by the grip tab 114. For example, the gripping feature 117 of FIG. 2 includes a plurality of straight raised ridges transverse to the grip tab 114, which ridges can improve a user's frictional grip on the grip tab 114. While in FIG. 2 the gripping feature 117 is located on the medical-device interface 115, in some embodiments, the gripping feature 117 can be positioned elsewhere. For example, the gripping feature 117 can be provided on the magnetizer interface 113 or both the medical-device interface 115 and the magnetizer interface 113 to further assist a user in holding the magnetizer cover 110. Indeed, as shown in FIGS. 4A and 4B, the gripping feature 117 can comprise a plurality of ridges on both the medical-device interface 115 and the magnetizer interface 113.

While the gripping feature 117 of FIG. 2 comprises a set of ridges, other patterns and forms of assistance can be used. For example, the gripping feature 117 can comprise a single ridge; ridges forming a predefined shape; or a dotted pattern. The gripping feature 117 can further be angled for facilitating a user's control of the magnetizer cover 110.

The magnetizer cover 110 further comprises the side barrier 120. The side barrier 120 can be positioned to abut a corresponding portion of the magnetizer 102, or other device, and thereby stabilize the magnetizer cover 110. In some embodiments, the magnetizer cover 110 can be manufactured for use with a corresponding magnetizer having a predetermined surface, and the side barrier 120 can have an angle, size and shape corresponding to the predetermined surface of the corresponding magnetizer so that, when the funnel stem 119 of the magnetizer cover 110 is inserted into the corresponding magnetizer, the side barrier 120 abuts the magnetizer surface. When the magnetizer cover 110 is inserted into the magnetizer 102 (e.g., via the funnel 116 or the funnel stem 119 thereof), the side barrier 120 can lean or rest on the magnetizer surface, thereby intervening between the medical device and the magnetizer to prevent inadvertent contamination of the medical device by touching the sterile side barrier 120 instead of the magnetizer 102. The magnetizer cover 110 is thereby stabilized by the magnetizer surface and protects from inadvertent contamination of the medical device by the magnetizer. While the side barrier 120 of FIG. 2 forms a curved edge with the base 112, and is at least substantially vertical and perpendicular to the base 112, in some embodiments, the side barrier 120 can be angled relative to the base 112. Furthermore, in some embodiments, the side barrier 120 can form other kinds of edges with the base 112 (e.g., a sharp edge).

In some embodiments, the magnetizer cover 110 and one or more of its components are sterilized. In some embodiments, the magnetizer cover 110 can be used with the magnetizer 102 when the magnetizer is not sterilized. A user can insert the magnetizer cover 110 into the unsterilized magnetizer 102, place an unmagnetized medical device (e.g., a unmagnetized needle) into the funnel mouth 118 of the magnetizer cover 110, and thereby magnetize the medical device without potentially exposing the needle to the unsterilized magnetizer 102.

Any or all components of the magnetizer cover 110, such as the base 112, the grip tab 114, the gripping feature 117, the funnel 116, or the side barrier 120, can be sterilized. For example, the side barrier 120 can be sterilized and act as a sterile barrier to protect a needle from an adjacent, unsterilized surface of the magnetizer 102. In some embodiments, the only surfaces of the magnetizer cover 110 that will touch the potentially contaminating magnetizer 102 will be those that the medical device will not, or is unlikely to, contact. Furthermore, a user can hold the sterilized grip tab 114 to insert the magnetizer cover 110 into the magnetizer 102 so as to avoid touching unsterile portions of the magnetizer 102. For example, the magnetizer cover 110 can be manufactured for use with a corresponding magnetizer having a cover interface configured to receive the magnetizer cover 110, which cover interface the magnetizer cover 110 rests on after insertion. In some embodiments, the grip tab 114 can have a length extending beyond the surface of the magnetizer 102 so that a user can use sterile gloves to hold a portion of the grip tab 114 which does not touch the magnetizer 102 after the magnetizer cover 110 has been inserted, and thus avoid contaminating the sterile gloves.

In some embodiments, the funnel stem 119 is hollow. For example, the funnel stem 119 can be at least substantially free from structures which would impede the passage of a medical device (e.g., needle) therethrough.

Figure 3:
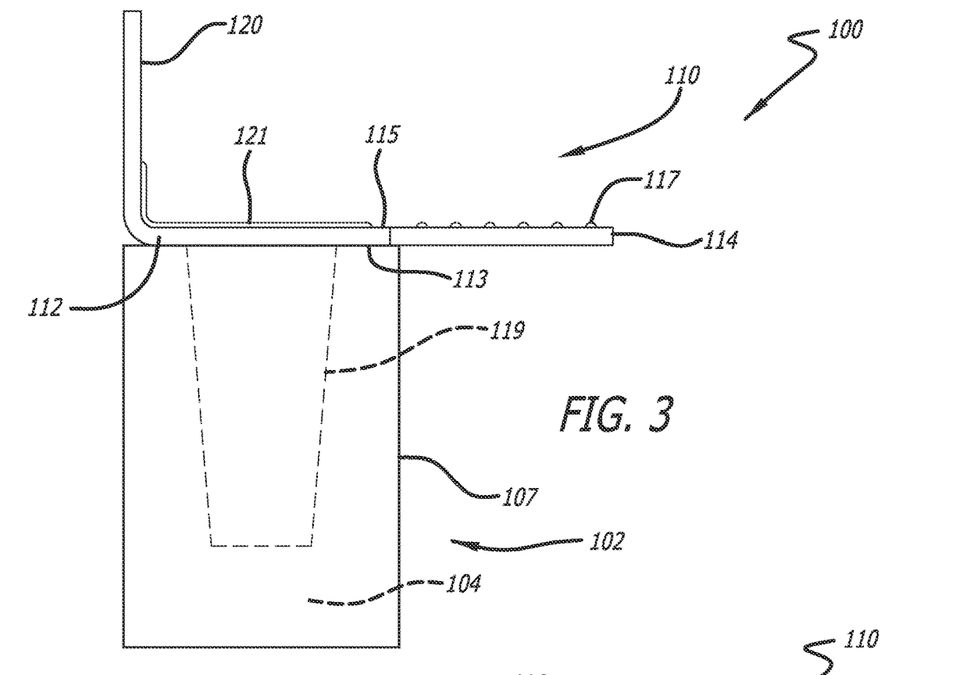
FIG. 3 illustrates a side view of the magnetization system in accordance with some embodiments.

Referring to FIG. 3, a side view of the magnetizer cover 110 with the magnetizer 102 is illustrated in accordance with some embodiments. In the embodiment of FIG. 3, the magnetizer cover 110 includes the funnel 116, the funnel stem 119 of which is inserted into the magnetizer 102 so that the funnel stem 119 is positioned in the magnetizer chamber 104. Medical devices (e.g., needles) inserted into the funnel 116 are thereby protected from contact with the magnetizer chamber 104.

Furthermore, the magnetizer cover 110 includes a magnetizer interface 113 positioned on the magnetizer 102. Before and during insertion of the medical device into the funnel 116, the magnetizer interface 113 prevents a medical device from accidentally contacting the magnetizer 102.

In the embodiment of FIG. 3, the grip tab 114 can be held by a user to position the magnetizer cover 110 on the magnetizer 102. The side barrier 120 extends from the medical-device interface 115 to aid the user in positioning the magnetizer cover 110, and to protect nearby potentially contaminated surfaces (e.g., on the magnetizer 102).

Referring to FIG. 4A, a top view of the magnetizer cover 110 is illustrated in accordance with some embodiments. The grip tab 114 includes the gripping feature 117 on the medical-device interface 115 to assist a user in holding the grip tab 114. The funnel mouth 118 can be used to insert a medical device for magnetization. The side barrier 120 extends to aid a user in positioning the magnetizer cover 110. A user with sterile gloves can hold the grip tab 114 to allow placing the magnetizer cover 110 inside the magnetizer 102 while maintaining glove sterility. Referring to FIG. 4B, a bottom view of the magnetizer cover 110 is illustrated in accordance with some embodiments. The magnetizer cover 110 includes the magnetizer interface 113. As set forth above, the grip tab 114 can further include the gripping feature 117 on the magnetizer interface 113 to further assist a user in holding the grip tab 114. A medical device can pass through the funnel stem 119 for magnetization.

Figure 5A:
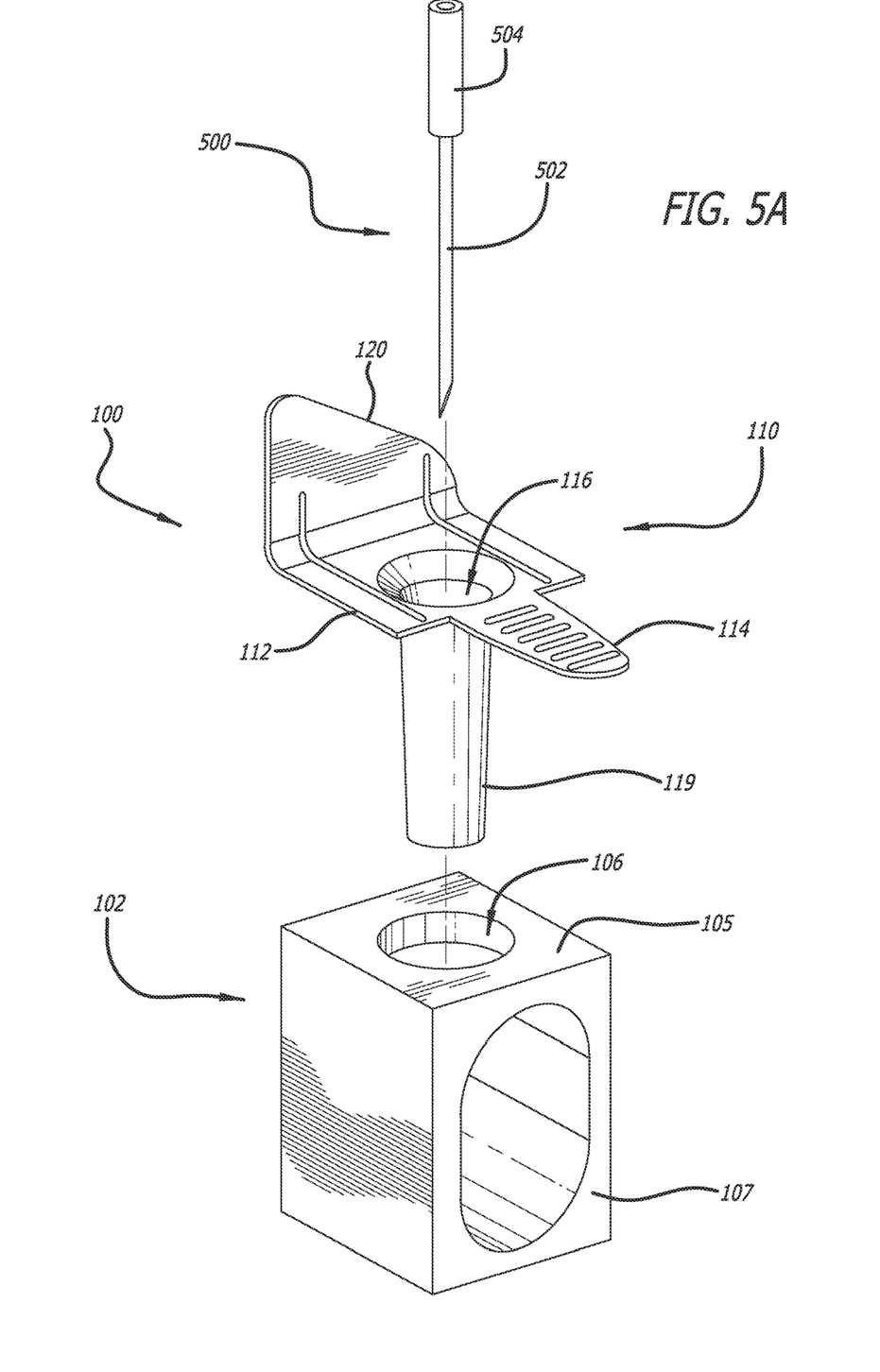
FIG. 5A illustrates an exploded view of a needle and the magnetization system in accordance with some embodiments.
Figure 5B:
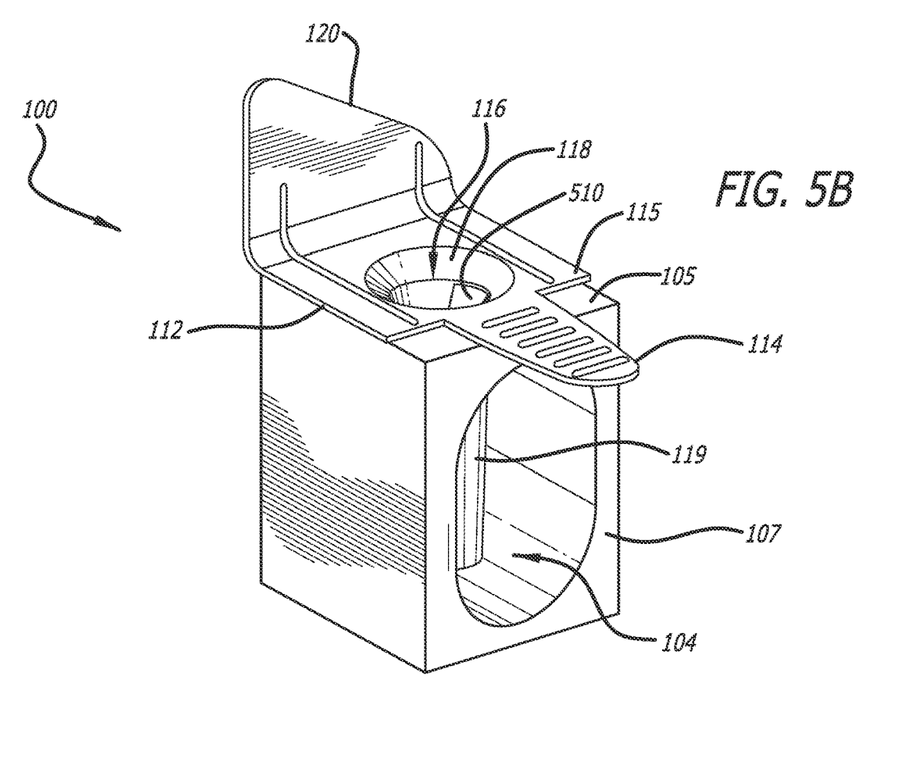
FIG. 5B illustrates a perspective view of the magnetization system including a first needle cover-removing feature in accordance with some embodiments.

Referring to FIG. 5A, an exploded view of a needle and the magnetization system 100 including the magnetizer cover 110 and the magnetizer 102 is shown in accordance with some embodiments. Additionally, FIG. 5B illustrates the magnetization system of FIG. 5A including the magnetizer cover 110 inserted into the magnetizer 102 and the needle inserted into the funnel stem 119 of the needle cover in accordance with some embodiments. The magnetization system 100 includes the magnetizer cover 110 and the magnetizer 102, where the magnetizer cover 110 is specifically configured to be inserted into an opening of the magnetizer 102 such that the funnel 116, including the funnel stem 119 thereof, extends into the magnetizer 102. Further, the funnel stem 119 is configured to receive a needle, such as the needle 500 (which can include a magnetizable portion 502 and a non-magnetizable portion 504) of FIGS. 5A-5B, where the needle 500 progresses or advances within the funnel stem 119 in order to be magnetized by the magnetizer 102.

In some embodiments, the magnetizer cover 110 includes the base 112 and the funnel 116, where the funnel 116 can include a tapered cylindrical portion that extends away from the funnel mouth 118, which is referred to herein as the funnel stem 119. In the embodiment of FIG. 5A the funnel stem 119 can be inserted through the magnetizer aperture 106 of the magnetizer 102. The magnetizer cover 110 can be placed on the magnetizer 102 using the grip tab 114. The magnetizer 102 then securely retains the magnetizer cover 110 as shown in FIG. 5B. In some embodiments in which the funnel stem 119 is the tapered cylindrical structure, the funnel stem 119 can have a diameter that is less than a diameter of the magnetizer aperture 106; thus, the funnel stem 119 is configured to pass therethrough and be received by the magnetizer 102.

The magnetizer cover 110 includes the side barrier 120 which can align with a surface of the magnetizer 102. The side barrier 120 can stabilize the magnetizer cover 110 as well as prevent potentially contaminating portions of the magnetizer 102 from contacting those portions of the magnetizer cover 110 which can be in contact with a magnetizable medical device.

In some embodiments, each portion and component of the magnetizer cover 110 can be sterilized. For example, in the embodiments of FIGS. 5A-5B the grip tab 114 can be sterilized so that a user with sterilized gloves is not contaminated by contact thereof. Furthermore, the interior (not shown) of the funnel 116 is sterilized so that a sterile medical device placed within will not be contaminated.

Figure 5C:
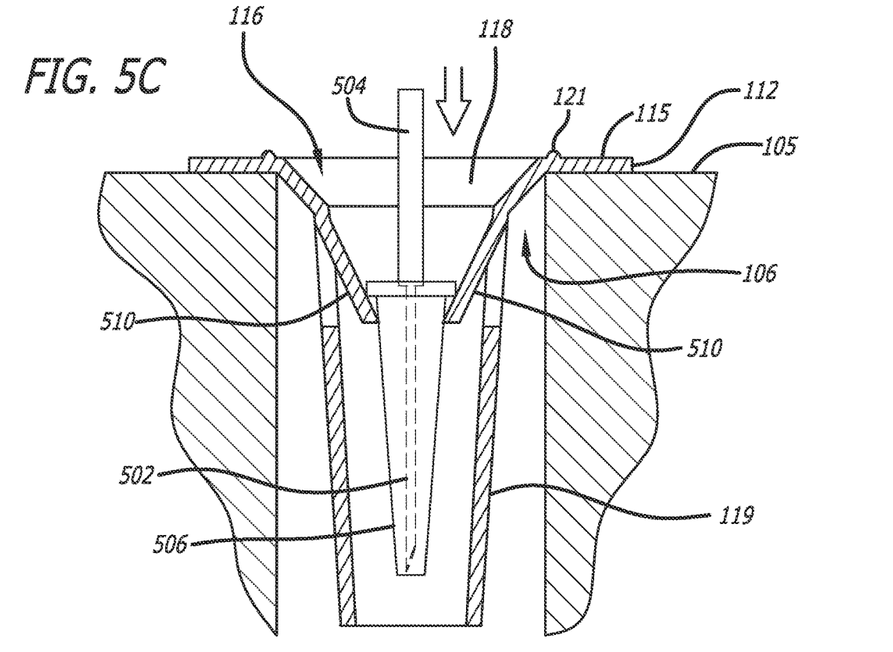
FIG. 5C illustrates a cross-sectional view of the needle with the first needle cover thereover being inserted into the magnetization system in accordance with some embodiments.
Figure 5D:
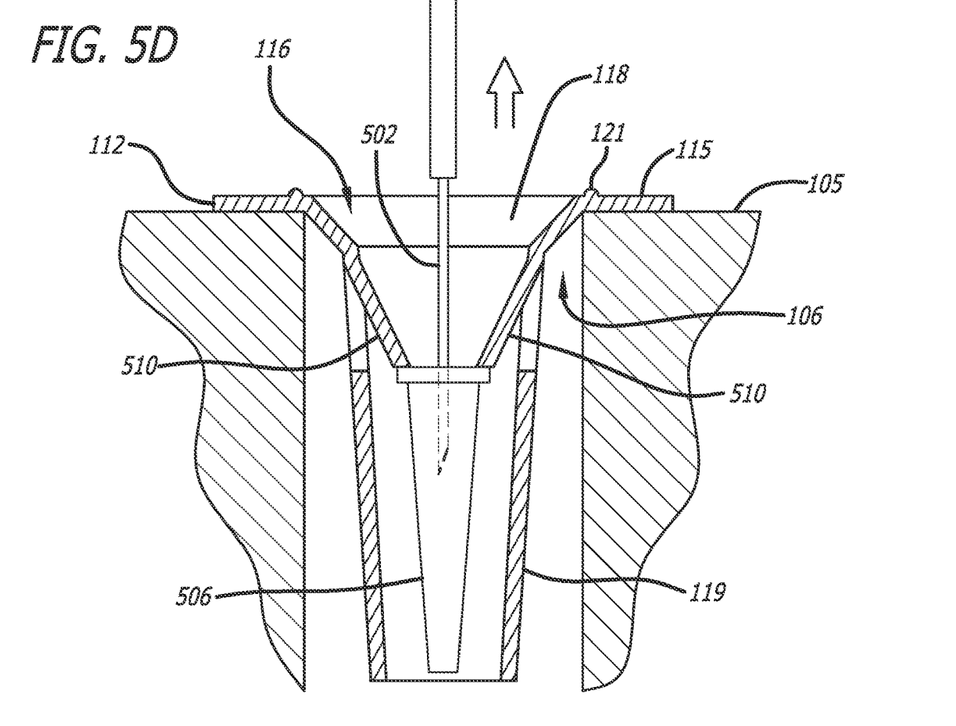
FIG. 5D illustrates a cross-sectional view of the needle being withdrawn from the magnetization system leaving the first needle cover therein in accordance with some embodiments.
Figure 5E:
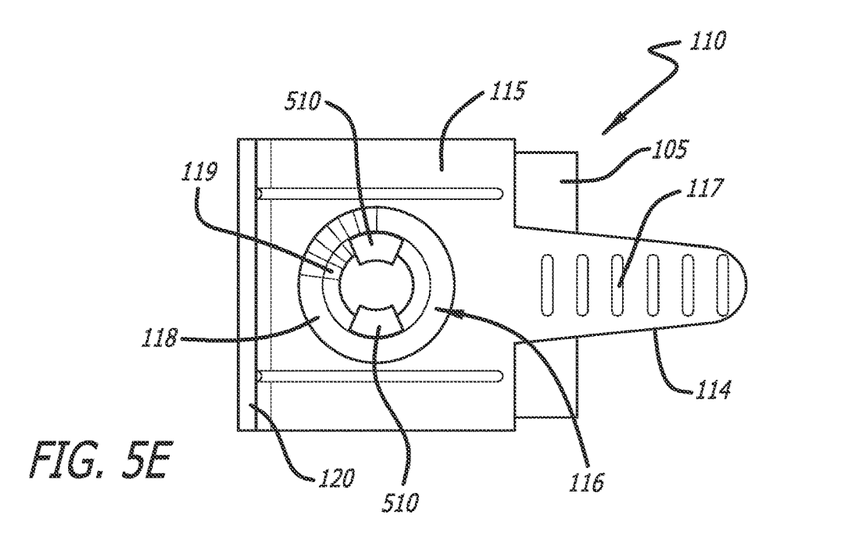
FIG. 5E illustrates a top view of the magnetization system of FIGS. 5C and 5D in accordance with some embodiments.

Referring now to FIGS. 5C-5E, the magnetizer cover 110 can include one or more inwardly facing prongs 510 within the funnel 116 or the funnel stem 119 thereof near the funnel mouth 118 or even extending from the funnel mouth 118 into the funnel stem 119. It can be advantageous to insert the needle 500 including a needle cover 506 into the magnetizer 102, e.g., to maintain safety and sterility. The one-or-more prongs 510 can serve to contact the needle cover 506 and once the needle cover 506 has been inserted past the one-or-more prongs 510, catch the needle cover 506 and prevent the needle cover 506 from exiting the magnetizer cover 110 through the funnel mouth 118. Thus, a clinician can insert the needle 500 with the needle cover 506 thereover to magnetize the needle 500, then remove the needle 500 while simultaneously withdrawing the needle 500 from the needle cover 506. In some embodiments, the funnel 116 can have an open end (e.g., an open end of the funnel stem 119 opposite the funnel mouth 118) thereby enabling removal of the needle cover 506. The open end can optionally include a removable cover as discussed above. In some embodiments, the magnetizer cover 110 can include a closed end of the funnel stem 119 and be disposed after a single use along with the needle cover 506.

Figure 5F:
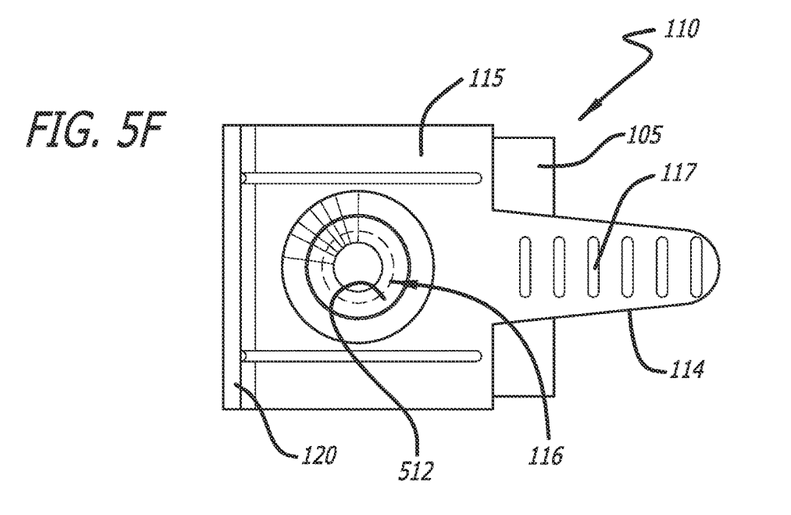
FIG. 5F illustrates a perspective view of the magnetization system including a second needle cover-removing feature in accordance with some embodiments.

Referring now to FIG. 5F, similar to the embodiment of FIGS. 5C-5E, the magnetizer cover 110 can include a continuous, inwardly angled ring 512 within the funnel 116 or the funnel stem 119 thereof but near the funnel mouth 118. The ring 512 can operate in the same manner as the prong embodiment of FIGS. 5C-5E.

Figure 6:
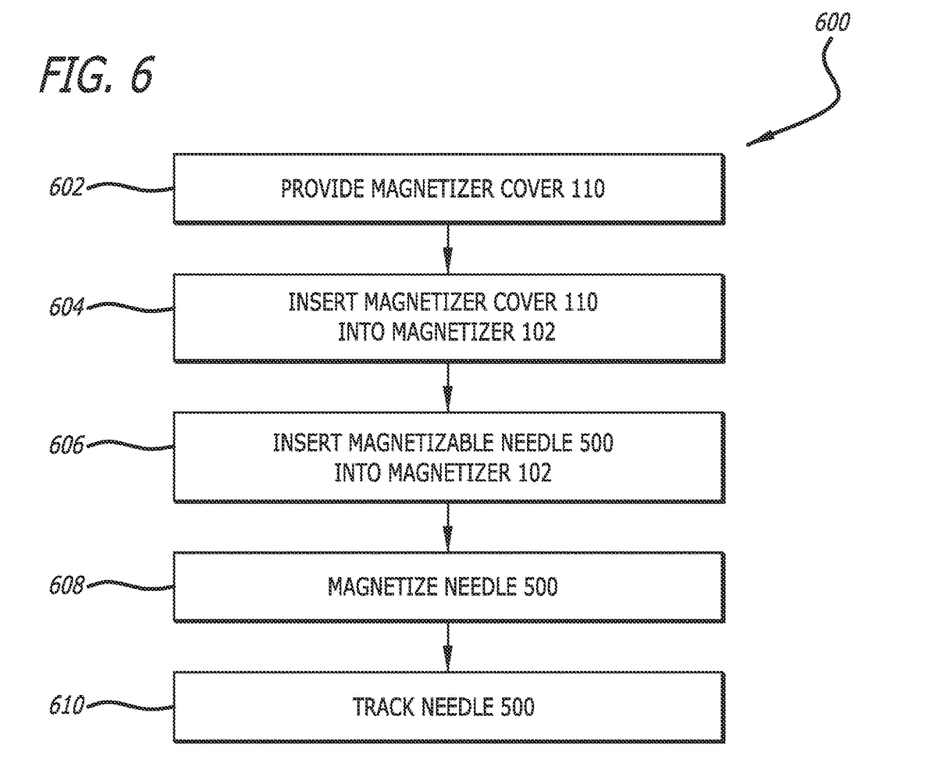
FIG. 6 illustrates a method of the magnetization system in accordance with some embodiments.

Referring now to FIG. 6, a method 600 can include maintaining sterility of an elongate medical device such as the needle 500 while magnetizing the medical device. The method 600 comprises a plurality of operations illustrated by the blocks of FIG. 6, where one or more operations can be optional. The method 600 can begin when the magnetizer cover 110 is provided (block 602). Next, a magnetizer cover-applying operation (block 604) can include inserting at least the funnel stem 119 of the magnetizer cover 110 into the magnetizer aperture 106 of the magnetizer 102, thereby disposing the funnel stem 119 in the magnetization chamber 104 of the magnetizer 102. A subsequent medical device-inserting operation (block 606) can include inserting a magnetizable portion of the medical device such as the magnetizable portion 502 of the needle 500 into the funnel stem 119 of the magnetizer cover 102. As set forth herein, the funnel stem 119 is configured to protect the magnetizable portion of the medical device from contacting the magnetizer 102. A magnetization-initiating operation includes initiating magnetization of the medical device such that the magnetizable portion of the medical device (e.g., the magnetizable portion 502 of the needle 500) is magnetized by the magnetizer 102 (block 608).

While not shown, the method 600 can further include a medical device-withdrawing operation. The medical device-withdrawing operation includes withdrawing the medical device from the funnel stem 119 after magnetization of the medical device is complete. If the medical device includes a cover thereover (e.g., the needle 500 with the needle cover 506), the one-or-more prongs 510 or the ring 512 catch the cover during the medical device-inserting operation when inserting the magnetizable portion of the medical device into the funnel stem. The one-or-more prongs 510 or the ring 512 also prevent the cover from being withdrawn from the funnel stem 119 with the medical device, thereby retaining the cover in the funnel stem 119 following the medical device-withdrawing operation. Whether or not the one-or-more prongs 510 or the ring 512 is present in the magnetizer cover 102, following the medical device-withdrawing operation, the magnetized medical device (e.g., the magnetized needle 500), which has remained sterile throughout the entire method 600, can be inserted into a patient's body, where the insertion can be tracked, such as by an ultrasound-imaging system, due to the magnetization of the medical device (block 610).

Ultrasound-Imaging Systems

In some embodiments, a magnetic-based device guidance system can be an ultrasound imaging system. In some embodiments, the ultrasound-imaging system can include a console, a display screen, an ultrasound probe, and the magnetizer 102. In some embodiments, an ultrasound imaging system can further include the magnetizer cover 110. An ultrasound-imaging system can be used to image a target such as a blood vessel or an organ within a body of a patient prior to a percutaneous puncture with a medical device (e.g., needle) for inserting the needle into the target and accessing the target. Ultrasound-imaging systems can be used with a variety of ultrasound-based medical procedures, such as catheterization or to perform a biopsy of patient tissue. During use of the ultrasound imaging system, the clinician can need to reach out of a sterile field around the patient to control the ultrasound-imaging system. In some embodiments, the display screen can be used to display the distance and orientation of a magnetized medical device such as a needle. Distance and orientation data can be superimposed in real-time atop an ultrasound image of the target, thus enabling a clinician to accurately guide the magnetized medical device to the intended target In some embodiments, the ultrasound probe is coupled to the console. The probe can be placed against a skin surface to generate ultrasound signals into a patient, receive reflected ultrasound signals or ultrasound echoes from the patient by way of reflection of the generated ultrasonic pulses by the body of the patient, and convert the reflected ultrasound signals into corresponding electrical signals for processing into ultrasound images by the console to which the ultrasound probe is communicatively coupled. In this way, a clinician can employ the ultrasound-imaging system to determine a suitable insertion site and establish vascular access with the needle or another medical device.

In some embodiments, an ultrasound probe can include a magnetic-sensor array for detecting a magnetized medical device such as a needle during ultrasound-based medical procedures. The magnetic-sensor array includes a number of magnetic sensors embedded within or included on a housing of the ultrasound probe. The magnetic sensors are configured to detect a magnetic field or a disturbance in a magnetic field as magnetic signals associated with the magnetized medical device when it is in proximity to the magnetic-sensor array. The magnetic sensors are also configured to convert the magnetic signals from the magnetized medical device (e.g., the needle) into electrical signals for the console to process into distance and orientation information for the magnetized medical device with respect to the predefined target, as well as for display of an iconographic representation of the magnetized medical device on the display screen. Thus, the magnetic-sensor array enables the ultrasound-imaging system to track the needle or the like. The magnetic sensors can include three orthogonal sensor coils for enabling detection of a magnetic field in three spatial dimensions. In some embodiments, instead of 3-D sensors, a plurality of 1-dimensional ("1-D") magnetic sensors can be included and arranged as desired to achieve 1-, 2-, or 3-D detection capability.

During operation of the ultrasound-imaging system, the ultrasound probe is placed against skin of the patient. An ultrasound beam is produced so as to ultrasonically image a portion of a target such as a blood vessel beneath a surface of the skin of the patient. The ultrasonic image of the blood vessel can be depicted and stabilized on the display screen of the ultrasound-imaging system.

The ultrasound-imaging system can be configured to detect the distance and orientation of a medical device, such as by way of the magnetic sensors. By way of example, the magnetic-sensor array of the ultrasound probe is configured to detect a magnetic field of the magnetized medical device or a disturbance in a magnetic field due to the magnetized magnetic device. Each magnetic sensor of the magnetic sensors in the magnetic-sensor array is configured to spatially detect the needle in 3-dimensional space. Thus, during operation of the ultrasound-imaging system, magnetic field strength data of the medical device's magnetic field sensed by each magnetic sensor of the magnetic sensors is forwarded to a processor of the console, which computes in real-time the distance and orientation of the magnetized medical device. The distance and orientation of the magnetized medical device is also for graphical display on the display screen.

The distance or orientation of any point along an entire length of the magnetized medical device in a coordinate space with respect to the magnetic-sensor array can be determined by the ultrasound-imaging system using the magnetic-field strength data sensed by the magnetic sensors. Moreover, a pitch and yaw of the needle can also be determined. Suitable circuitry of the ultrasound probe, the console, or other components of the ultrasound-imaging system can provide the calculations necessary for such distance or orientation.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures can be made from the particular embodiments disclosed herein without departing from the scope of the concepts provided herein.

What is claimed is:

1. A magnetizer cover for maintaining sterility of a medical device while magnetizing the medical device, comprising:
   a base including a medical-device interface and a magnetizer interface opposite the medical-device interface, the base including at least a planar portion;
   a funnel extending from the base, the funnel including a funnel stem configured to protect an elongate medical device from contacting a magnetizer when the medical device is inserted into the funnel, wherein the planar portion extends circumferentially around the funnel; and
   a grip tab extending from the base configured for manipulating the magnetizer cover.

2. The magnetizer cover of claim 1, wherein at least the base includes one or more structural stability ridges incorporated therein to provide added structural stability to the magnetizer cover.

3. The magnetizer cover of claim 2, wherein the grip tab extends from the base in a same direction as the one or more structural stability ridges incorporated into the base.

4. The magnetizer cover of claim 1, wherein the base and the funnel are configured to intervene between the magnetizer and the medical device to prevent the medical device from touching the magnetizer and contaminating the medical device.

5. The magnetizer cover of claim 1, further comprising:
   a side barrier orthogonal to the base, the side barrier configured to intervene between the magnetizer and the medical device to prevent the medical device from touching the magnetizer and contaminating the medical device.

6. The magnetizer cover of claim 5, wherein the grip tab extends from the base opposite the side barrier.

7. The magnetizer cover of claim 1, wherein the funnel extends from the magnetizer interface of the base enabling the funnel stem to insert into a magnetizer aperture of the magnetizer.

8. The magnetizer cover of claim 1, wherein the funnel further includes a funnel mouth between the base and the funnel stem, the funnel mouth configured to direct the medical device into the funnel stem.

9. The magnetizer cover of claim 1, wherein a length of the funnel is greater than a length of a magnetizable portion of the medical device.

10. The magnetizer cover of claim 1, wherein the funnel stem has an open end opposite the base.

11. The magnetizer cover of claim 1, wherein the funnel stem has a closed end opposite the base.

12. The magnetizer cover of claim 8, wherein the funnel stem includes one or more inwardly facing prongs extending into the funnel stem from the funnel mouth, the one or more prongs configured to catch a cover over the medical device when the medical device is inserted into the funnel with the cover thereover and prevent the cover from being withdrawn from the funnel when the medical device is withdrawn from the funnel.

13. The magnetizer cover of claim 1, wherein the grip tab includes a plurality of transverse ridges on a same face as the medical-device interface of the base.

14. The magnetizer cover of claim 13, wherein the grip tab further includes the plurality of transverse ridges on a same face as the magnetizer interface of the base.

15. A magnetizing system for maintaining sterility of a medical device while magnetizing the medical device, the magnetizing system comprising:
   a magnetizer, including:
      a magnetizer aperture formed in a cover interface of the magnetizer; and
      a magnetization chamber accessible through the magnetizer aperture; and
   a magnetizer cover, including:
      a base including a medical-device interface and a magnetizer interface opposite the medical-device interface, the base including at least a planar portion;
      a funnel extending from the base, the funnel including a funnel stem configured to protect an elongate medical device from contacting the magnetizer when the medical device is inserted into the funnel, wherein the planar portion extends circumferentially around the funnel; and
      a grip tab extending from the base configured for manipulating the magnetizer cover.

16. The magnetizing system of claim 15, wherein at least the base includes one or more structural stability ridges incorporated therein to provide added structural stability to the magnetizer cover.

17. The magnetizing system of claim 16, wherein the grip tab extends from the base in a same direction as the one or more structural stability ridges incorporated into the base.

18. The magnetizing system of claim 15, wherein the base and the funnel are configured to intervene between the magnetizer and the medical device to prevent the medical device from touching the magnetizer and contaminating the medical device.

19. The magnetizing system of claim 15, further comprising:
- a side barrier orthogonal to the base, the side barrier configured to intervene between the magnetizer and the medical device to prevent the medical device from touching the magnetizer and contaminating the medical device.

20. The magnetizing system of claim 19, wherein the grip tab extends from the base opposite the side barrier.

21. The magnetizing system of claim 15, wherein the funnel extends from the magnetizer interface of the base enabling the funnel stem to insert into the magnetizer aperture of the magnetizer.

22. The magnetizing system of claim 15, wherein the funnel further includes a funnel mouth between the base and the funnel stem, the funnel mouth configured to direct the medical device into the funnel stem.

23. The magnetizing system of claim 15, wherein a length of the funnel is greater than a length of a magnetizable portion of the medical device.

24. The magnetizing system of claim 15, wherein the funnel stem has an open end opposite the base.

25. The magnetizing system of claim 15, wherein the funnel stem has a closed end opposite the base.

26. The magnetizing system of claim 22, wherein the funnel stem includes one or more inwardly facing prongs extending into the funnel stem from the funnel mouth, the one or more inwardly facing prongs configured to catch a cover over the medical device when the medical device is inserted into the funnel with the cover thereover and prevent the cover from being withdrawn from the funnel when the medical device is withdrawn from the funnel.

27. The magnetizing system of claim 15, wherein the grip tab includes a plurality of transverse ridges on a same face as the medical-device interface of the base.

28. The magnetizing system of claim 27, wherein the grip tab further includes the plurality of transverse ridges on a same face as the magnetizer interface of the base.

* * * * *